US00PP22257P2

(12) United States Plant Patent
Pavlich

(10) Patent No.: US PP22,257 P2
(45) Date of Patent: Nov. 15, 2011

(54) ***HEUCHERA* PLANT NAMED 'GINGER PEACH'**

(50) Latin Name: *Heuchera spp.*
Varietal Denomination: Ginger Peach

(76) Inventor: John C. Pavlich, Olympia, WA (US)

( * ) Notice: Subject to any disclaimer, the term of this patent is extended or adjusted under 35 U.S.C. 154(b) by 0 days.

(21) Appl. No.: 12/806,931

(22) Filed: Aug. 23, 2010

(51) Int. Cl.
*A01H 5/00* (2006.01)

(52) U.S. Cl. ..... Plt./440

(58) Field of Classification Search ..... Plt./440
See application file for complete search history.

*Primary Examiner* — Annette Para
(74) *Attorney, Agent, or Firm* — Klarquist Sparkman, LLP

(57) ABSTRACT

A new and distinct *Heuchera* plant substantially as shown and described, characterized by ruffled leaves, peach colored spring leaves with a light veil, ginger to rose amber summer and winter leaves, a medium large plant size, and excellent vigor.

1 Drawing Sheet

Botanical denomination: *Heuchera* spp.
Variety designation: 'Ginger Peach'.

The present invention relates to a new and distinct cultivar of *Heuchera* and given the cultivar name of 'Ginger Peach'. *Heuchera* is in the family Saxifragaceae. *Heuchera* 'Ginger Peach' originated from an OP cross in Olympia, Wash. using *Heuchera* 'Ginger Ale' (U.S. Plant Pat. No. 18,173) as the seed parent. This seedling was selected for its foliage color, hardiness, and vigor.

Compared to the seed parent, *Heuchera* 'Ginger Ale', the new cultivar is larger and has leaves that are undulate, darker, and flowers that are creamy white rather than ginger.

Compared to *Heuchera* 'Marmalade' (U.S. Plant Pat. No. 15,945), the new cultivar has a tighter habit, shorter flowers, and foliage with rose and peach tones rather than amber.

This new *Heuchera* is distinguished by:

1. peach colored spring leaves with a light veil,
2. ginger to rose amber summer and winter leaves,
3. medium large plant size,
4. ruffled leaves,
5. and excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two year old *Heuchera* 'Ginger Peach' in the trial field in flower in early June in Canby, Oreg.

FIG. 2 shows the same plant in September in Canby, Oreg.

DETAILED PLANT DESCRIPTION

The following is a detailed description of the new *Heuchera* cultivar based on observations of two-year-old specimens grown in the garden in full sun in June in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—23 cm tall from top of the foliage to the ground and 46 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Basal.
*Shape.*—Ovate to orbicular.
*Lobing /division.*—5 main lobes, with 2 to 3 secondary lobes.
*Venation.*—Palmate.
*Margins.*—Crenate and undulate.
*Apex.*—Mucronulate.
*Base.*—Cordate, overlapping.
*Blade size.*—Grows to 10 cm long and 9.7 cm wide.
*Surface texture.*—Both sides glandular.
*Petiole description.*—Grows to 16 cm long and 3 mm wide, glandular hairs, Greyed Purple 187C.
*Leaf color.*—Spring, top side, Greyed Purple 184A with veil White N155B, bottom side Greyed Purple 187D; summer topside Greyed Orange 175A with veil N155A.

Inflorescence:

*Size.*—Grows to 4 cm wide and 19 cm long.
*Type.*—Thyrse.
*Number of flowers per thyrse.*—About 70 per thyrse.
*Number of thyrse.*—About 7 in first spring bloom.
*Peduncle.*—Grows to 10 cm tall and 3 mm wide at base, Greyed Purple 187B, glandular hairs, with 3 or more petiolate leaves (ovate, blades grow to 3 cm long and 2.5 cm wide, 5 lobed with the terminal lobe the longest, margin serrate, Greyed Orange 174B on top and Greyed Purple 184A on bottom side).

*Pedicel.*—Variable in size, with glandular hairs, Greyed Purple 187B.

*Bloom period.*—Mid June in Canby, Oreg.

Flower bud:

*Size.*—2 mm wide and 3 mm long.

*Description.*—Glandular puberulent, ovoid.

*Color.*—Top ⅓ White N155B to bottom ⅔ Greyed Purple 184D.

Flower:

*Type.*—Perfect.

*Shape.*—Campanulate.

*Size.*—4 mm long and 3 mm wide.

*Petal description.*—5 in number, 3 mm long, spatulate with a clawed base, reflexed, tip acute, margin entire, glabrous on both sides, White NN155C on both sides.

*Calyx description.*—4 mm long and 3 mm wide, with 5 overlapping lobes, divided ½ way to the base, glandular hairs on both sides, tip mucronulate, margin entire, both sides White NN155A on top ⅔ and Greyed Red 182d on bottom ⅓.

*Stamen description.*—5 in number, 2 mm long, filaments 1.5 mm long, White NN155B, anthers Greyed Orange 174D, no pollen, male sterile.

*Pistil description.*—One central two beaked pistil, 4.5 mm long, ovary 1.5 mm long and Yellow Green 144C, style 3 mm long , White NN155B.

*Fragrance.*—None.

*Lastingness.*—Each thyrse blooms for about 2 weeks on the plant

Fruit:

*Type.*—Two beaked capsule.

*Size.*—5.5 mm deep and 2 mm wide.

*Fertility.*—Good.

*Color.*—Greyed Brown 199A.

Seed:

*Shape.*—Linear.

*Size.*—2 mm long.

*Color.*—Black, RHS 202A.

Disease and pest tolerance: No known resistances. Excellent disease tolerance to powdery mildew and *Heuchera* rust. All *Heuchera* are susceptible to root weevils.

I claim:

1. A new and distinct *Heuchera* plant as herein illustrated and described.

* * * * *

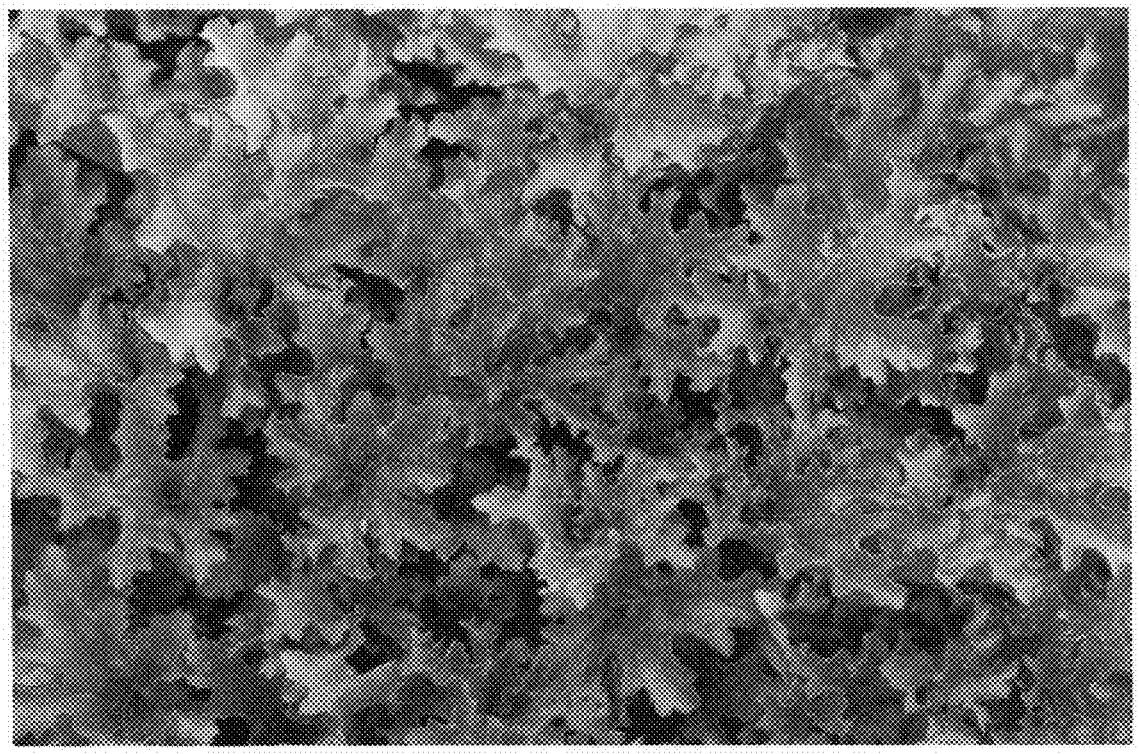

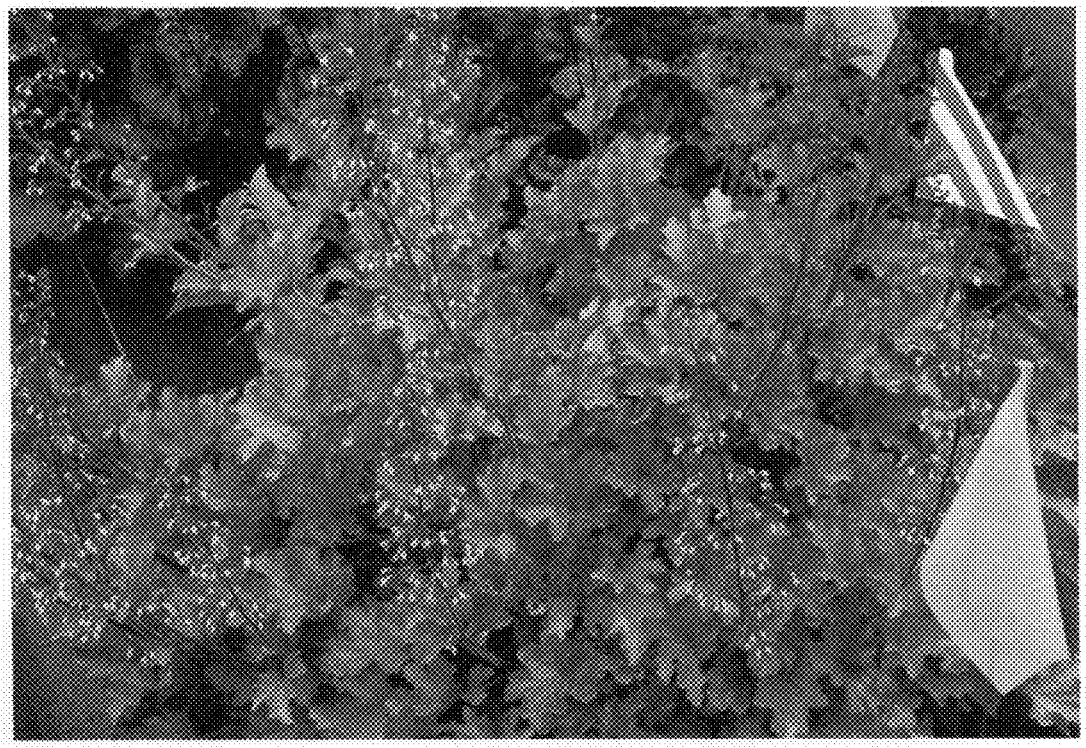
Figure 1 above. Figure 2 below.